US010663453B2

(12) United States Patent
Gouldy et al.

(10) Patent No.: US 10,663,453 B2
(45) Date of Patent: May 26, 2020

(54) RECOVERY TEST DEVICE AND METHOD OF DETERMINING IF A HUMAN BODY IS NUTRITIONALLY RECOVERED FROM AN ENDURANCE EVENT

(71) Applicant: URINEBALANCE LLC, Riviera Beach, FL (US)

(72) Inventors: Kathleen Gouldy, Superior, CO (US); Simon Borucki, Riviera Beach, FL (US)

(73) Assignee: Jeffrey S. Melcher, Boca Raton, FL (US)

( * ) Notice: Subject to any disclaimer, the term of this patent is extended or adjusted under 35 U.S.C. 154(b) by 257 days.

(21) Appl. No.: 15/857,843

(22) Filed: Dec. 29, 2017

(65) Prior Publication Data

US 2018/0188232 A1 Jul. 5, 2018

Related U.S. Application Data

(60) Provisional application No. 62/440,756, filed on Dec. 30, 2016.

(51) Int. Cl.

| | |
|---|---|
| ***G01N 33/493*** | (2006.01) |
| ***A61B 5/145*** | (2006.01) |
| ***A61B 5/20*** | (2006.01) |
| *G01N 33/483* | (2006.01) |
| *G01N 33/48* | (2006.01) |
| *A61B 5/154* | (2006.01) |
| *A61B 10/00* | (2006.01) |

(52) U.S. Cl.

CPC ....... *G01N 33/493* (2013.01); *A61B 5/14507* (2013.01); *A61B 5/20* (2013.01); *A61B 10/007* (2013.01); *A61B 2503/10* (2013.01)

(58) Field of Classification Search

CPC ............. G01N 33/493; G01N 33/4833; G01N 33/483; G01N 33/48; G01N 33/00; A61B 5/1507; A61B 5/145; A61B 5/00; A61B 5/20; A61B 10/007; A61B 2503/10

USPC ............................................ 436/172; 422/50

See application file for complete search history.

(56) References Cited

U.S. PATENT DOCUMENTS 4,076,502 A * 2/1978 Dugle ...................... C12Q 1/26 422/420
5,260,219 A * 11/1993 Fritz ........................ A61B 5/00 435/12
9,311,520 B2 * 4/2016 Burg ................ G01N 35/00029

FOREIGN PATENT DOCUMENTS

EP 0 029 915 * 7/1983 ............. G01N 33/64

OTHER PUBLICATIONS

Hydra Trend Urine Test Strips, 28 Smallwood St, Underwood QLD 4119, pp. 1-2, 2016.
True Plus, produced by Nipro Diagnostics' Ketone Care, http://trividiahealth.com/our_products/ts_ketone.aspx, pp. 1-2, 2016.
Ketone test 14 is sold under the tradename Ketostix® by Bayer, www.ketostix.net, pp. 1-2, 2016.
Multisix® by Siemens, https://www.healthcare.siemens.com/point-of-care-testing/urinalysis-products/urinalysis-reagents/multistix-10-sg-reagent-strips, pp. 1-5, 2016.
URS-11 by Med Lab Diagnostics, https://www.medlabdiagnosticssupplies.com/, pp. 1-2, 2016.
RE-008 by Real Doctors, https://www.amazon.ca/Real-Doctors-Urinalysis-Parameters-Professional/dp/B01JZO9KR0, also at https://realdoctorsshop.com/products/realdoctors-litmus-paper-ph-test-and-urine-test-strips-with-e-book, pp. 1-2, 2016.
-Hooper, "Water-loss (intracellular) dehydration assessed using urinary tests: how well do they work? Diagnostic accuracy in older people," Am. J. Clin. Nutr 2016: 104:121-31, 2016, American Society for Nutrition.
Sommerfield, "Validity of Urine Specific Gravity When Compared to Plasma Osmolality as a Measure of Hydration Status in Male and Female NCAA Collegiate Atheletes," J. Strength Cond. Res. Aug. 2016: 30(8): 2219-2225.
Zubac, "Urine Specific Gravity as an Indicator of Dehydration in Olympic Combat Sport Athletes: considerations for research and practice," Eur J. Sport Sci, Aug. 2018: 18(7): 920-929, Epub May 10, 2018.

* cited by examiner

*Primary Examiner* — Christine T Mui
(74) *Attorney, Agent, or Firm* — Jeffrey S. Melcher; Melcher Patent Law PLLC

(57) ABSTRACT

Provided is a device for determining whether a human is fully nutritionally recovered from an endurance event having a ketone indicator and ketone test for measuring the amount of ketones in urine and a specific gravity indicator and specific gravity test for measuring the specific gravity of urine. Also provided is a method using the device to determine whether a human is fully nutritionally recovered from an endurance event.

20 Claims, 3 Drawing Sheets

RECOVERY TEST DEVICE AND METHOD OF DETERMINING IF A HUMAN BODY IS NUTRITIONALLY RECOVERED FROM AN ENDURANCE EVENT

FIELD OF THE INVENTION

The invention relates to a device and method for determining whether a human body is nutritionally recovered from an endurance event, prior to initiating the athlete's next training session or an athletic event.

BACKGROUND OF THE INVENTION

Endurance events usually last at least one hour and often times multiple hours. Examples of endurance events include hiking, running, biking, swimming, and athletic events, both competitively and training. Athletic events include races, games, and other competitions.

During an endurance event, humans sweat and can easily become dehydrated. Keeping hydrated and recovering properly are vital to training in an optimal state of health. Most endurance athletes are accustomed to feeling somewhat depleted. Often times, the workouts are intended to have the athlete struggling by the finish. Travel, altered sleep patterns, dietary changes, altitude, humidity levels, medications, and personal stressors can impact daily balance tremendously. Even if life is under control, it can be tough to truly know if one has properly nutritionally recovered from a workout or athletic event and ready to begin the next one.

Training in a dehydrated state can lead to a multitude of problems from minor to life threatening. These include exhaustion, electrolyte imbalances, gastrointestinal disturbances, headaches, kidney stones, muscular injuries, altered mental status, spasms, shock, seizures, psychoses, and even death. Endurance athletes are accustomed to suffering and often times there is a fine line between safe and unstable. Also, an athlete new to a distance or event will not be familiar with "how they should feel." Athletes often guess at whether they have fully nutritionally recovered from an endurance event.

Most of the tools and tests that have been utilized are anecdotal and largely subjective, such as:

1) Looking at the color of the urine;
   - Subjectively compare day to day
   - Urine color charts (extremely limited, difficult to individualize)
2) Salivary flow;
3) Physical Assessment;
   - Look in the mirror for changes in physique
   - Weight change on scale
4) Body Mass Scale;
5) Blood tests;
   - Invasive/painful, expensive, unable to complete at home, lengthy result times
   - Plasma osmolality+total body water is medical gold standard
6) Medical grade urine test strips; and
   - Able to test at home, fast results, expensive
   - Assess 10 parameters (usually technical and confusing for the lay person)
   - Ketone test strip: single parameter assessing for the presence of ketones in urine,
7) Refractrometry of Urine;
   - Device to measure urine specific gravity (now automated, yet expensive).

There is currently no simple and reliable method for determining whether athletes have fully nutritionally recovered from an endurance event.

SUMMARY OF THE INVENTION

An objective of the invention is to provide simple and reliable device and method for determining whether athletes have fully nutritionally recovered from an endurance event. In the present invention the urine specific gravity is used to assess for hydration and the presence of ketones in the urine are used to indicate that there is evidence of fat and/or muscular breakdown. If either of the ketone test or the specific gravity test are not within the desired ranges nutritional supplementation would need to continue to fully nutritionally recover before training or competing.

The objectives of the invention can be obtained by a device for determining whether a human body has nutritionally recovered from an endurance event comprising:

- a support;
- a ketone test on the support for measuring an amount of ketones in urine when the ketone test is contacted with the urine;
- a ketone indicator on the support that indicates whether the amount of ketones in the urine is within a desired ketone range;
- a specific gravity test on the support for measuring the specific gravity of the urine when the specific gravity test is contacted with the urine; and
- a specific gravity indictor on the support that indicates whether the specific gravity is within a desired specific gravity range, wherein the human body is in a nutritionally recovered state when the amount of ketones in the urine is within the desired ketone range and the specific gravity of the urine is within the desired specific gravity range.

Objectives of the invention can also be obtained by a method of determining whether a human body has nutritionally recovered from an endurance event comprising the steps of:

- providing the device for determining whether a human body has nutritionally recovered from an endurance event;
- contacting the ketone test and the specific gravity test with urine from the human body; and
- reading the device to determine whether the body is nutritionally recovered from an endurance event, wherein the human body is in a nutritionally recovered state when the amount of ketones in the urine is within the desired ketone range and the specific gravity of the urine is within the desired specific gravity range.

DETAILED DESCRIPTION OF THE INVENTION

Figure 1:
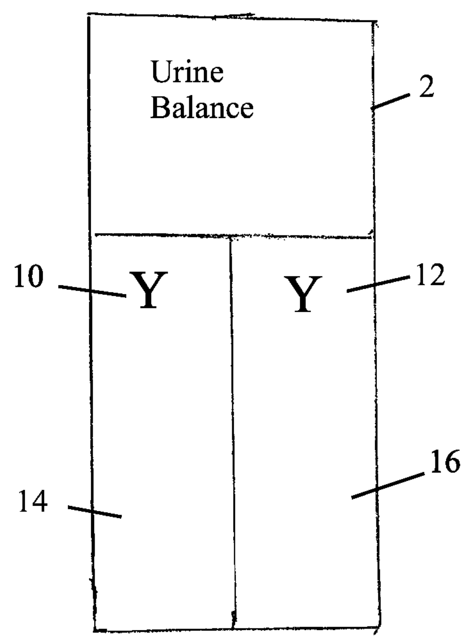
FIG. 1 illustrates a device according to the present invention.
Figure 2:
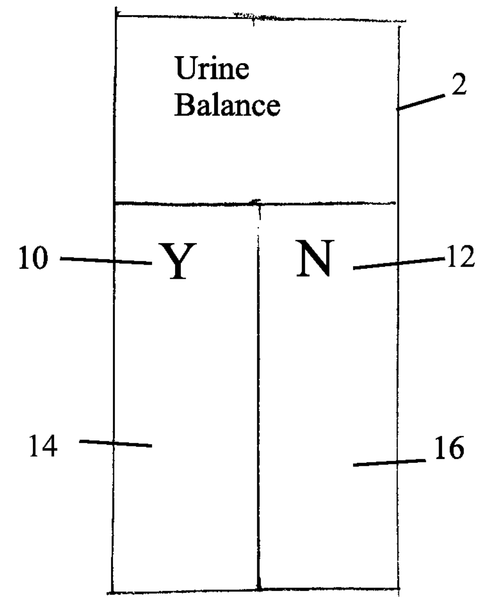
FIG. 2 illustrates a device according to the present invention.
Figure 3:
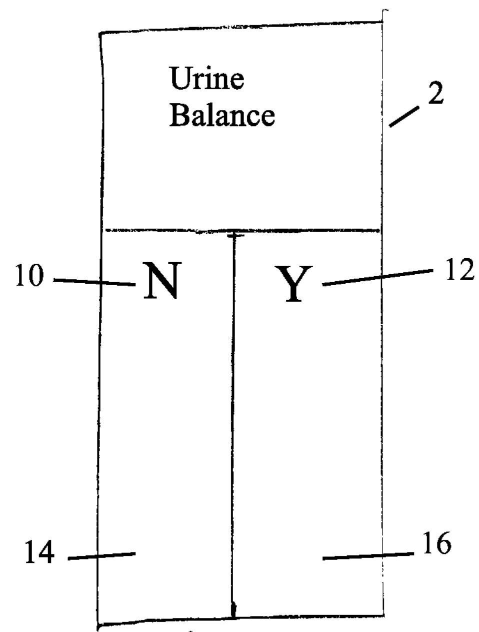
FIG. 3 illustrates a device according to the present invention.
Figure 4:
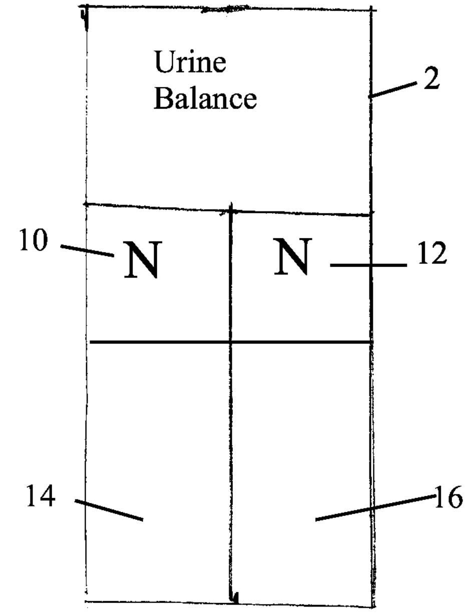
FIG. 4 illustrates a device according to the present invention.

The invention will be explained with reference to the attached non-limiting FIGS. 1-12. The FIGS. 1-12 illustrate embodiments of the device 2, which can be used to quickly and efficiently determine whether the human body has been fully nutritionally recovered from an endurance event. The device comprises a support 2, a ketone test 14, a specific gravity test 16, a ketone indicator 10 that indicates the amount of ketones present in the urine when urine is applied to the ketone test 14, and a specific gravity indictor 12 that indicates whether the specific gravity is within a desired specific gravity range when urine is applied to the specific gravity test 16. The support 2 can be formed from any suitable material, including those materials used for urine test strips, such as plastic and/or paper. Plastic strips can have pads impregnated with chemicals that react with the compounds present in the urine producing a characteristic color. For the paper strips, the chemicals can be absorbed directly into the paper. The support 2 can be biodegradable. The support 2 is preferably formed from a continuous paper or plastic as shown in the Figs.

The ketone indicator 10 can be used to provide an indication of when the ketone concentration in the urine is within a desired ketone range. The ketone indicator 10 can comprise a color, range of colors, or symbols such as Y, N, –, or +. A desired ketone range is undetectable up to trace amounts, i.e. 5 mg/dl or less, and preferably the amount of ketones in the urine is undetectable. When color is utilized, after the urine is applied to the ketone test 14, the color of the ketone test 14 is compared to the color of the ketone indicator 10 and if the colors match then the ketone concentration in the urine is within the desired ketone range. When multiple colors are utilized as the ketone indicator 10 to provide a color range, a color on the ketone test 14 within the color range indicates that the amount of ketones in the urine is within the desired ketone range. When symbols are utilized, after the urine is applied to the ketone test 14, a symbol (indicator 10) can appear to identify whether the ketone concentration of the urine is within the desired ketone range.

The specific gravity indicator 12 can be used to provide an indication of when the specific gravity of the urine within a desired specific gravity range. The specific gravity indicator 12 can comprise a color, range of colors, or symbols such as Y, N, –, or +. A desired specific gravity range is less than 1.030, preferably 1.000 to 1.020, and more preferably from 1.000-1.015. When color is utilized, after the urine is applied to the specific gravity test 16, the color of the specific gravity test 16 is compared to the color of the specific gravity indicator 12 and if the colors match then the specific gravity in the urine is within the desired specific gravity range. When multiple colors are utilized as the specific gravity indicator 12 to provide a color range, a color on the specific gravity test 16 within the color range indicates that the specific gravity of the urine is within the desired specific gravity range. When symbols are utilized, after the urine is applied to the specific gravity test 16, a symbol (indicator 12) will appear to identify whether the specific gravity of the urine is within the desired specific gravity range.

The term nutritionally recovered is defined as the athlete being in an optimal hydration/re-hydration state, without signs of nutritional depletion or breakdown of fat and/or muscle in the urine.

FIGS. 1-4 illustrate examples of the device 2 in which the ketone indicator 10 and the specific gravity indicator 12 are symbols Y for within desired ranges and N for outside desired ranges for the amount of ketones and the specific gravity.

FIGS. 5-10 illustrate examples of the device 2 in which the ketone indicator 10 and the specific gravity indicator 12 are colors that identify whether the amount of ketones and the specific gravity are within the desired ranges.

Figure 11:
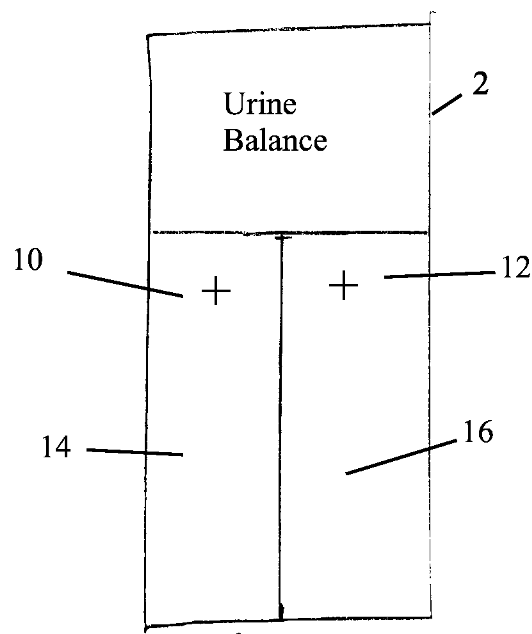
FIG. 11 illustrates a device according to the present invention.
Figure 12:
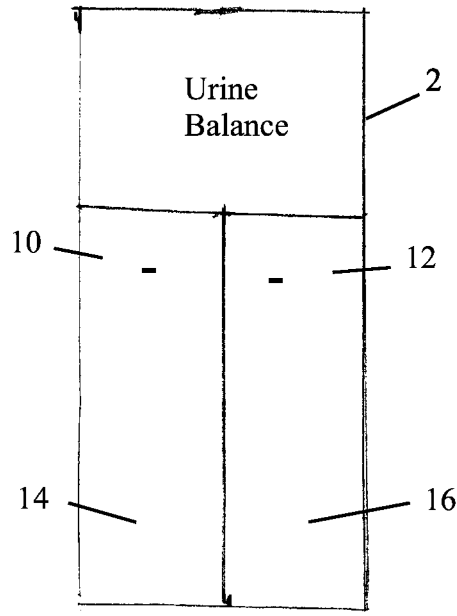
FIG. 12 illustrates a device according to the present invention.

FIGS. 11 and 12 illustrate examples of the device 2 in which the ketone indicator 10 and the specific gravity indicator 12 are symbols + within desired ranges and – for outside desired ranges for the amount of ketones and the specific gravity.

Figure 5:
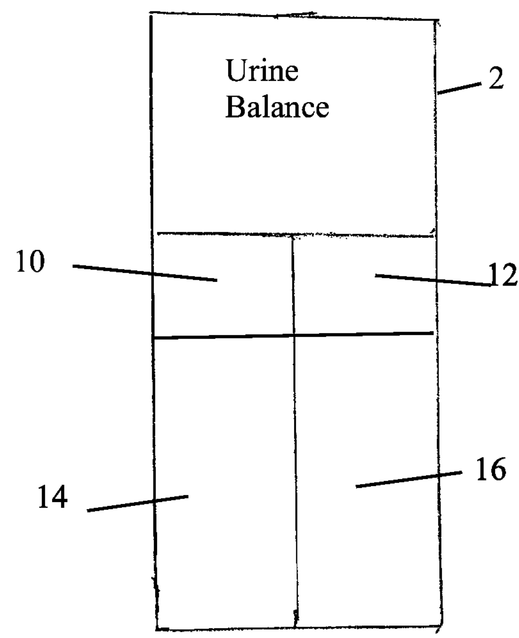
FIG. 5 illustrates a device according to the present invention.
Figure 6:
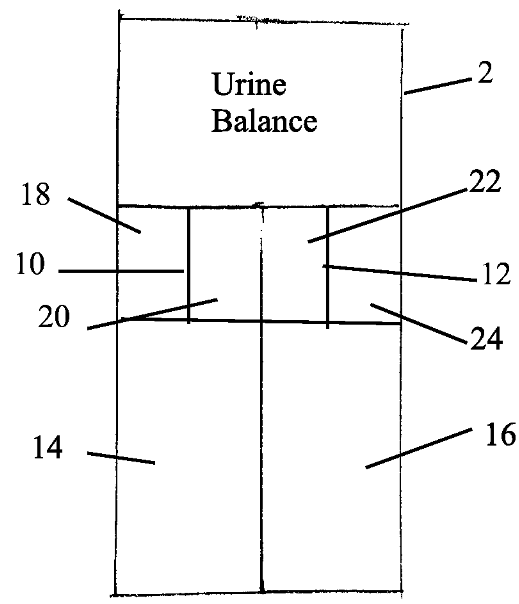
FIG. 6 illustrates a device according to the present invention.
Figure 7:
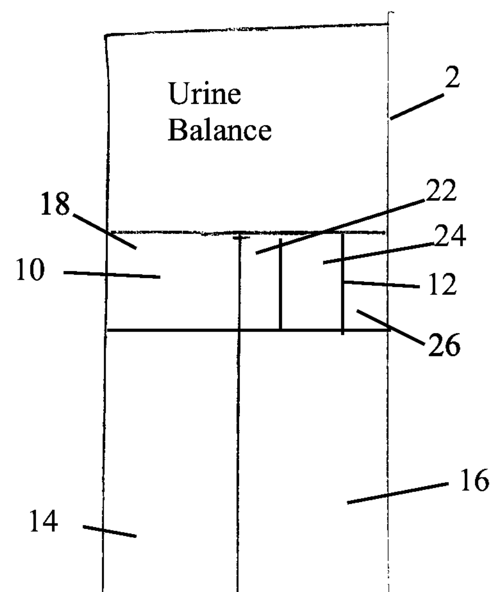
FIG. 7 illustrates a device according to the present invention.
Figure 8:
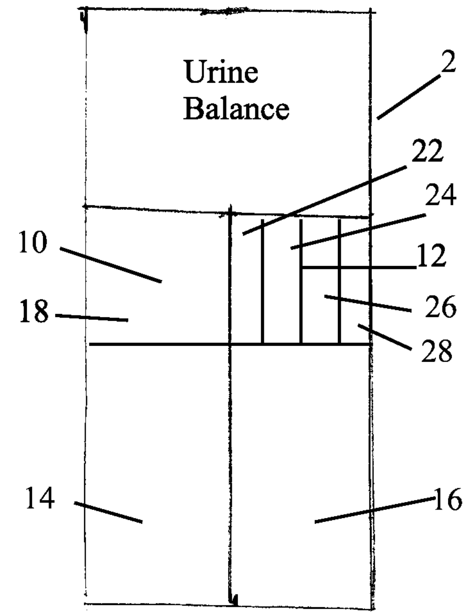
FIG. 8 illustrates a device according to the present invention.
Figure 9:
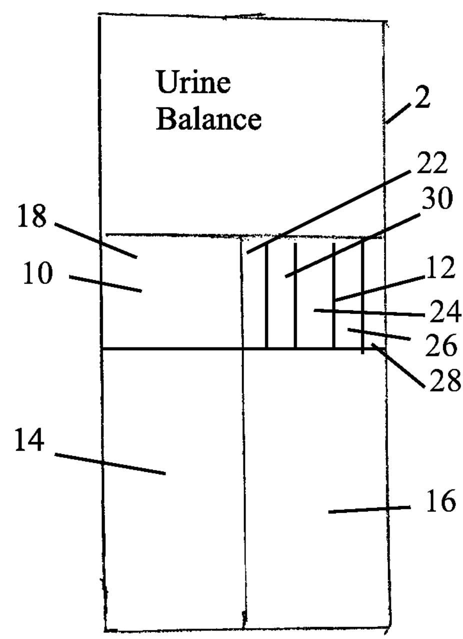
FIG. 9 illustrates a device according to the present invention.
Figure 10:
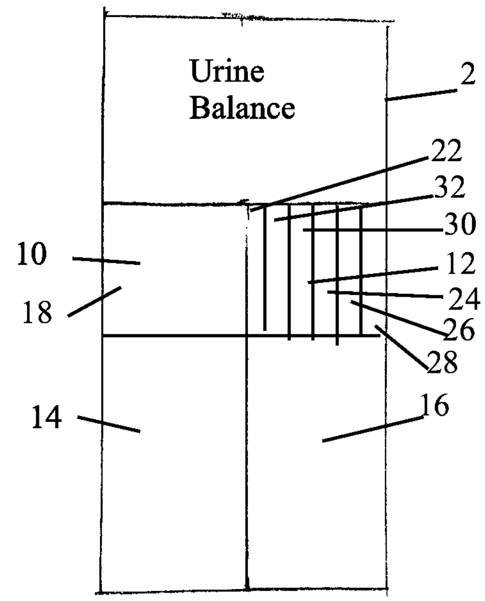
FIG. 10 illustrates a device according to the present invention.

FIG. 5 illustrates an example where a single color for the indicator 10 and a single color for the indicator 12 are utilized. FIG. 6 illustrates an example where a color 18 for no detectible ketones and a color 20 for trace amounts of ketones and a color 22 for a specific gravity of 1.000 are utilized. FIG. 7 illustrates an example where the color 18 for no detectable ketones, a color 22 for a specific gravity of 1.000, a color 24 for a specific gravity of 1.015, and a color 26 for a specific gravity of 1.020 are utilized. FIG. 8 illustrates an example where the color 18 for no detectable ketones, a color 22 for a specific gravity of 1.000, a color 24 for a specific gravity of 1.015, a color 26 for a specific gravity of 1.020, and a color 28 for a specific gravity of 1.025 are utilized. FIG. 9 illustrates an example where the color 18 for no detectable ketones, a color 22 for a specific gravity of 1.000, a color 30 for a specific gravity of 1.010, a color 24 for a specific gravity of 1.015, a color 26 for a specific gravity of 1.020, and a color 28 for a specific gravity of 1.025 are utilized. FIG. 10 illustrates an example where the color 18 for no detectable ketones, a color 22 for a specific gravity of 1.000, a color 32 for a specific gravity of 1.005, a color 30 for a specific gravity of 1.010, a color 24 for a specific gravity of 1.015, a color 26 for a specific gravity of 1.020, and a color 28 for a specific gravity of 1.025 are utilized.

An example of a commercially available chemical system suitable for use in the present invention on the specific gravity test 16 is sold under the tradename HydraTrend™ by Uridynamics. The specific gravity tests 16 can contain the chemical system that changes color, usually within 30-60 seconds.

For example, the specific gravity test 16 can be based on the change in dissociation constant ($pK_a$) of an anionic polyelectrolyte (poly-(methyl vinyl ether/maleic anhydride)) in an alkali medium that is ionised and releases hydrogen ions in proportion to the number of cations present in the solution. The greater the cation concentration of the urine the more hydrogen ions are released, thereby reducing the pH. The specific gravity test 16 can also include bromothymol blue which measures this change in pH. In this instance, the colors can vary from dark blue with a reading of 1.000 to yellow for a reading of 1.030. The specific gravity test 16 can permit the determination of urine specific gravity between 1.000 and 1.030, within 0.005 with values obtained with the refractive index method. For increased accuracy, 0.005 maybe added to readings from urine with pH equal to or greater than 6.5. Elevated specific gravity readings can be obtained in the presence of moderate quantities (1-7.5 g/L) of protein. The specific gravity of urine is a measurement of the density of urine; the relative proportions of dissolved solids in relationship to the total volume of the specimen. Specific gravity reflects how concentrated or diluted a sample may be. Water has a specific gravity of 1.000. Urine will always have a value greater than 1.000 depending upon the amount of dissolved substances (salts, minerals, etc.) that may be present. Very dilute urine has a low specific gravity value and very concentrated urine has a high value. Specific gravity measures the ability of the kidneys to concentrate or dilute urine depending on fluctuating conditions. A normal specific gravity range is 1.005-1.030, and an average range is 1.010-1.025. Low specific gravity can be associated with conditions like diabetes insipidus, excessive water intake, diuretic use or chronic renal failure.

An example of a commercially available chemical system suitable for use in the present invention in the ketone test 14 is sold under the tradename True Plus, produced by Nipro Diagnostics' Ketone Care™. The reagent detects as little as 5-10 mg/dl acetoacetic (ketones) in urine. The ketone test 14 can contain the chemical reagent that changes in color. Exemplary reagents are 7.6% w/w Sodium Nitroprusside, 92.4% Buffer and Nonreactive ingredients. Another example of a commercially available chemical system suitable for use in the present invention in the ketone test 14 is sold under the tradename Ketostix® by Bayer.

Further examples of commercially available chemical systems suitable for use in the ketone test 14 and the specific gravity test 16 are sold under the tradename Multisix® by Siemens; URS-11 by Med Lab Diagnostics; RE-008 by Real Doctors; and SpeedyTests.

EXAMPLES

Example 1

The inventors struggled with hydration this past summer while training in South Florida. On one occasion, they set out at 8:30 pm, each carrying nine pounds of water. They each had completely emptied their hydration packs over 20 miles, sucked on a few water fountains, and still each lost approximately seven pounds. Their program called for them to get back out running within 24 hours. However, they did not know if our bodies were truly ready to get back at training. Simon is an Emergency Physician who has suffered from kidney stones in the past. Kathleen is an orthopedic nurse practitioner who has endured a host of overuse injuries. Even with their running experience and medical knowledge, they still had difficulty assessing their hydration status. They searched for a way to make our recovery more predictable, and found that there is a significant void in this arena. The results of their search is described in the background section.

We have found that monitoring urine specific gravity and ketone presence with one device provides an inexpensive, noninvasive, and simple means of detecting optimal recovery in an endurance athlete. Monitoring trends can become an integral component of an athlete's training and nutritional program. The combination of these two indicators on one testing strip for use in determining recovery from an endurance event has not been found available in the American market.

Example 2

On Saturday, 24 Dec. 2016, an athlete named Scott completed a triathlon training workout comprising of a four hour road bike followed by a 90 minute run. The weather was cool and cloudy, and he was able to fuel (drink and eat) according to his plan throughout the workout. He was tired, as expected, following the workout, but did not feel ill at all. To assess his hydration/nutritional status and to obtain a baseline "recovery" status he voided on a UrineBalance strip. The test revealed that he was "not recovered," as expected since the ketone and specific gravity readings were not within the desired ketone range and specific gravity range. Scott was mindful to eat and drink frequently, and consumed a large/healthy dinner meal. He went to bed feeling well and excited for his scheduled Sunday workout, another 90 minute tempo run followed by a 60 minute swim. On Sunday morning, he voided on another UrineBalance strip and it is determined that he had successfully rehydrated and refueled since the ketone and specific gravity readings were within the desired ketone range and specific gravity range. Thus, Scott completed Sunday's training in an optimal state, with an excellent performance.

While Scott's weekend training and recovery was ideal, it is certainly not the norm. Lets say that the following week, Scott had to travel for work and had a birthday celebration on Friday. His weekend training calender calls for another four intense activities. Also, the weather is warmer. He voids on Saturday morning and realizes that he is not in an optimal hydration state prior to the workout. His UrineBalance result gives him the information he needs to train safely and effectively. He postponed his workout and continued to recover (eat, drink, and rest) for the rest of the morning. He reassesses with another UrineBalance strip in the afternoon and it is determined that he is now in an optimal hydration & nutritional state. With UrineBalance, Scott has an added tool to keep him healthy and competitive.

Example 3

Inventor Simon Borucki is a Floridian who has grown up running and training year round in the South Florida heat. Simon is also an Emergency Medicine Physician who understands the importance of nutrition and hydration. Even with this knowledge, Simon has trained and even competed dehydrated and without adequate nutrition. Simon also suffer from painful kidney stones which can be precipitated by dehydration. UrineBalance (device according to present invention) has changed the way Simon thinks about hydration, nutrition and training. Since using the system he have been more aware of "nutrition," which simply provides the body fuel to work and muscles to repair and build. And, "hydration" which effects the heart's ability to pump oxygen and nutrient carrying blood to muscles, kidneys (regulating electrolytes) and skin (regulating body temperature).

During Simon's busy 12 hour ER shifts it is easy to forget to drink or even eat. In the past, he has trained after such shifts, as do many aspiring athletes and weekend warriors with full time jobs. This is not ideal. UrineBalance gives Simon a tool to help determine his level of recover before starting my next fitness routine and should make my workouts both safer and more productive.

The following are some examples of UrineBalance work day runs and more 6 mile run—70 F temp
Pre run: SG: 1.010 Ketones: neg
Post run: SG: 1.020 Ketones: neg
6 mile run—80 F temp
Pre run: SG 1.02 Ketone: neg
Post run: SG 1.03 Ketones trace
12 mile run—75 F temp
Pre run: SG 1.010 ketones: neg
Post run: SG 1.030 ketones: trace
7 mile run—65 F temp
Pre run: SG 1.015 ketones: neg
Post run: SG 1.025 ketones: neg
5 mile run—80 F temp
*weekend run post party the night before**
Pre run: SG 1.025 ketones: trace
Postponed run until later in the evening after hydrating and eating.
Pre run: SG 1.010 Ketone: neg
Post run: SG 1.025 Ketones: beg
6 mile run—75 F temp
*post 12 hr ER shift/work run**
Checked at end of shift: SG: 1.025 Ketones: (Dehydrated).
Rehydrated for 3 hrs and rechecked.
SG 1.010 ketones: neg (recovered).
Post run: SG: 1.015 ketones: neg It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, steps and/or embodiments, the invention is not intended to be limited to the particulars disclosed herein. Rather, the invention extends to all functionally equivalent structures, processes and uses, such as are within the scope of the appended claims. Those skilled in the art, having the benefit of the teachings of this specification, may affect numerous modifications thereto and changes may be made without departing from the scope and spirit of the invention.

The invention claimed is:

1. A device for determining whether a human body has nutritionally recovered and rehydrated from an endurance event comprising:
- a support;
- a ketone test on the support for measuring an amount of ketones in urine when the ketone test is contacted with the urine;
- a ketone indicator on the support that indicates the amount of ketones in the urine is within a ketone range of undetectable to trace amounts;
- a specific gravity test on the support for measuring the specific gravity of the urine when the specific gravity test is contacted with the urine; and
- a specific gravity indictor on the support that indicates the specific gravity is within a specific gravity range of 1.000 to less than 1.030, wherein the human body is in a rehydrated and nutritionally recovered state when the ketone indicator indicates that the amount of ketones in the urine is within the ketone range and specific gravity indicator indicates that the specific gravity of the urine is within the specific gravity range.

2. The device according to claim 1, wherein the specific gravity range is 1.000 to 1.020.

3. The device according to claim 1, wherein the specific gravity range is 1.000 to 1.015.

4. The device according to claim 1, wherein the ketone indicator comprises a color present on the support that matches a color the ketone test forms when contacted with urine having ketones within the ketone range.

5. The device according to claim 1, wherein the specific gravity indicator comprises a color present on the support that matches a color the specific gravity test forms when contacted with urine having a specific gravity within the specific gravity range.

6. The device according to claim 1, wherein the ketone indicator comprises a symbol that is exposed or forms when the ketone test is contacted with urine.

7. The device according to claim 1, wherein the specific gravity indicator is a symbol that is exposed or forms when the specific gravity test is contacted with urine.

8. The device according to claim 1, wherein the support comprises a strip of paper and/or plastic.

9. A method of determining that a human body has rehydrated and has nutritionally recovered from an endurance event comprising the steps of:
- providing a device for determining that a human body has rehydrated and has nutritionally recovered from an endurance event comprising:
  - a support;
  - a ketone test on the support for measuring an amount of ketones in urine when the ketone test is contacted with the urine;
  - a ketone indicator on the support that indicates the amount of ketones in the urine is within a ketone range of undetectable to trace amounts;
  - a specific gravity test on the support for measuring the specific gravity of the urine when the specific gravity test is contacted with the urine; and
  - a specific gravity indictor on the support that indicates the specific gravity is within a specific gravity range of 1.000 to less than 1.030;
- contacting the device with the urine from the human body after an endurance event;
- the ketone indicator indicating that the measured ketones are within the ketone range; and
- the specific gravity indicator indicating that the measured specific gravity is within the specific gravity range, wherein the body is nutritionally recovered and rehydrated after the endurance event.

10. The method according to claim 9, wherein the specific gravity range is 1.000 to 1.020.

11. The method according to claim 9, wherein the specific gravity range is 1.000 to 1.015.

12. The method according to claim 9, wherein the ketone indicator comprises a color and the ketone test turns to a color when contacted with the urine.

13. The method according to claim 9, wherein the specific gravity indicator comprises a color and the specific gravity test turns to a color when contacted with the urine.

14. The method according to claim 9, wherein the ketone indicator comprises a symbol and the ketone test displays the symbol when contacted with the urine indicating that the measured ketones are within the ketone range.

15. The method according to claim 9, wherein the specific gravity indicator comprises a symbol and the specific gravity test displays the symbol when contacted with the urine indicating that the measured specific gravity is within the specific gravity range.

16. The method according to claim 9, wherein the support comprises a strip of paper and/or plastic.

17. The method according to claim 9, wherein the endurance event comprises at least one of running, swimming or bicycling.

18. A method of determining that a human body has not rehydrate or is nutritionally recovered from an endurance event comprising the steps of:

providing a device comprising:

a support;

a ketone test on the support for measuring an amount of ketones in urine when the ketone test is contacted with the urine;

a ketone indicator on the support that indicates the amount of ketones in the urine is within a ketone range of undetectable to trace amounts;

a specific gravity test on the support for measuring the specific gravity of the urine when the specific gravity test is contacted with the urine; and a specific gravity indictor on the support that indicates the specific gravity is within a specific gravity range of 1.000 to less than 1.030;

contacting the device with the urine from the human body after an endurance event; and at least one of the ketone indicator not indicating that the measured ketones are within the ketone range or the specific gravity indicator not indicating that the measured specific gravity is within the specific gravity range, wherein the body is at least one of not nutritionally recovered or not rehydrated after the endurance event.

19. The method according to claim 18, wherein the specific gravity range is 1.000 to 1.020.

20. The method according to claim 18, wherein the specific gravity range is 1.000 to 1.015.

* * * * *